US007391510B2

(12) United States Patent  (10) Patent No.: US 7,391,510 B2
Ben-Tulila et al.  (45) Date of Patent: Jun. 24, 2008

(54) SYSTEM AND METHOD FOR INSPECTING PATTERNED DEVICES HAVING MICROSCOPIC CONDUCTORS

(75) Inventors: Raphael Ben-Tulila, Kiryat-Gat (IL); Emil Berladsky, Rehovot (IL); Ilya Leizerson, Rehovot (IL); Ofer Saphier, Rehovot (IL)

(73) Assignee: Orbotech Ltd, Yavne (IL)

( * ) Notice: Subject to any disclaimer, the term of this patent is extended or adjusted under 35 U.S.C. 154(b) by 249 days.

(21) Appl. No.: 11/339,835

(22) Filed: Jan. 26, 2006

(65) Prior Publication Data

US 2007/0171404 A1    Jul. 26, 2007

(51) Int. Cl.
*G01N 21/00*  (2006.01)
(52) U.S. Cl. .................................. 356/237.1; 356/237.5
(58) Field of Classification Search .... 356/237.1–237.6
See application file for complete search history.

(56) References Cited

U.S. PATENT DOCUMENTS

| | | | |
|---|---|---|---|
| 6,092,059 A * | 7/2000 | Straforini et al. ............... 706/14 |
| 6,256,093 B1 * | 7/2001 | Ravid et al. ............... 356/237.2 |
| 6,597,448 B1 * | 7/2003 | Nishiyama et al. ........ 356/237.4 |
| 6,731,384 B2 * | 5/2004 | Ohshima et al. .......... 356/237.2 |
| 6,763,130 B1 * | 7/2004 | Somekh et al. .............. 382/145 |
| 6,810,297 B2 | 10/2004 | Adin et al. |
| 6,876,445 B2 * | 4/2005 | Shibuya et al. ............ 356/237.2 |
| 6,922,482 B1 * | 7/2005 | Ben-Porath .................. 382/149 |
| 6,947,151 B2 | 9/2005 | Fujii et al. |
| 7,035,447 B2 * | 4/2006 | Take ........................... 382/145 |
| 7,242,467 B2 * | 7/2007 | Wienecke ................. 356/237.5 |
| 7,274,444 B2 * | 9/2007 | Furman et al. ........... 356/237.2 |
| 2002/0054704 A1 | 5/2002 | Smilansky et al. |

* cited by examiner

*Primary Examiner*—Sang Nguyen
(74) *Attorney, Agent, or Firm*—Sughrue Mion, PLLC

(57) ABSTRACT

An inspection system operative to inspect patterned devices having microscopic conductors, the system comprising a camera viewing a location of a candidate defect on a patterned substrate and acquiring thereat at least one image of the location, the camera defining an optical axis, the at least one image being illuminated by at least one illumination offset from the optical axis, the illumination being supplied along at least first and second axes of illumination that are mutually non-parallel in a plane corresponding to a plane of the patterned substrate, wherein a response to the illumination supplied along the first axis is differentiable from a response to the illumination supplied along the second axis and a defect classifier operative to receive the at least one image and to distinguish therewithin a candidate defect caused by a cut or a candidate defect caused by excess material, from one another and/or from other types of candidate defects.

30 Claims, 17 Drawing Sheets

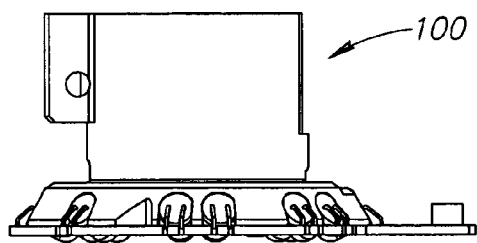
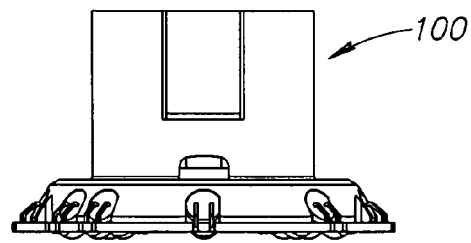
FIG.3A　　　　　　　　　FIG.3B
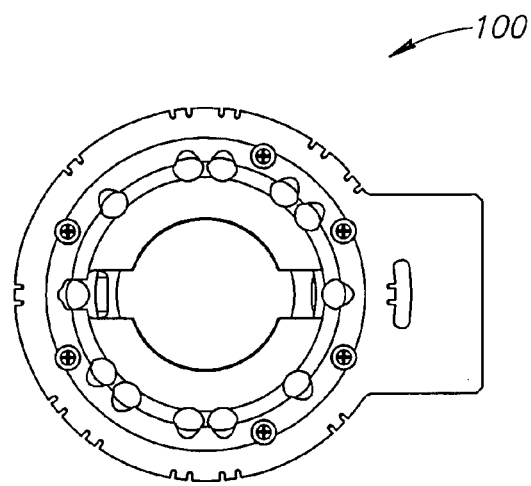
FIG.3C

| FEATURE | 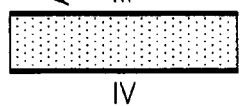 320 | 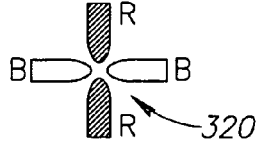 340 |
|---|---|---|
| 210 → III ▭ IV | III, IV ARE RED | III, IV ARE DARK |
| 220 → III ▯ IV | III, IV ARE BLUE | III, IV ARE DARK |
| 230 → III V, IV 240 VI | I, II ARE BLUE<br>III, IV, V, VI ARE RED | I, II ARE DARK<br>III, IV, V, VI ARE DARK |
| 250 → III IV, 260, V VI | I, II ARE RED<br>III, IV, V, VI ARE BLUE | III, IV, V, VI ARE DARK<br>I, II ARE DARK |
| 270 → 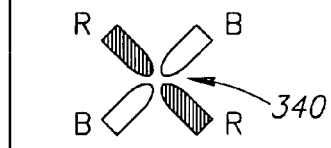 280, β₁ | FOR $0° \leq |\beta_1| \leq 15°$: I, II ARE BLUE, III–VI ARE RED<br>FOR $15° < |\beta_1| < 75°$: I–VI ARE DARK<br>FOR $75° \leq |\beta_1| \leq 90°$: I, II ARE RED, III–VI ARE BLUE | FOR $0° \leq |\beta_1| \leq 15°$: I–VI ARE DARK<br>FOR $15° < \beta_1 < 75°$: I, II ARE BLUE, III–VI ARE RED<br>FOR $-75° < \beta_1 \leq -15°$: I, II ARE BLUE, III–VI ARE RED<br>FOR $75° \leq |\beta_1| \leq 90°$: I–VI ARE DARK |

FIG.5A

| FEATURE | ![310](R B B R arrangement with 320) | ![330](R B arrangement with 340) |
|---|---|---|
| ![β₂ 294 292 diagram with III, IV, V, VI regions] | III, IV, V, VI ARE RED<br><br>FOR $0° \leq \beta_2 \leq 15°$: I, II ARE BLUE<br><br>FOR $15° < \beta_2 < 75°$: I, II ARE DARK<br><br><br><br>FOR $75° \leq \beta_2 \leq 90°$: I, II ARE RED | III, IV, V, VI ARE DARK<br><br>FOR $0° \leq \beta_2 \leq 15°$: I, II ARE DARK<br><br>FOR $15° < \beta_2 < 75°$: I, II ARE BLUE<br><br>FOR $-75° < \beta_2 < -15°$: I, II ARE RED<br><br>FOR $75° \leq |\beta_2| \leq 90°$: I, II ARE DARK |
| ![296 298 β₃ diagram with III, IV, V, VI regions] | III, IV, V, VI ARE BLUE<br><br>FOR $0° \leq |\beta_3| \leq 15°$: I, II ARE RED<br><br>FOR $15° < |\beta_3| < 75°$: I, II ARE DARK<br><br><br><br>FOR $75° \leq |\beta_3| \leq 90°$: I, II ARE BLUE | III, IV, V, VI ARE DARK<br><br>FOR $0° < |\beta_3| < 15°$: I, II ARE DARK<br><br>FOR $15° < |\beta_3| < 75°$: I, II ARE RED<br><br>FOR $-75° < \beta_3 < -15°$: I, II ARE BLUE<br><br>FOR $75° \leq |\beta_3| \leq 90°$: I, II ARE DARK |

FIG.5B

| 200 FEATURE | 310 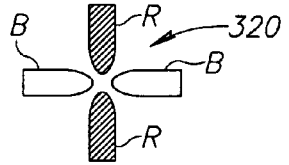 320 | 330 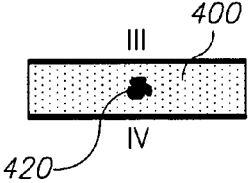 340 |
|---|---|---|
| 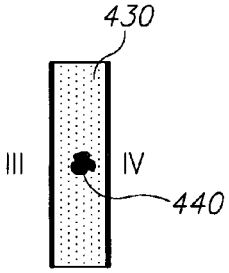 400, 420 (III, IV) | III, IV ARE RED<br>DUST IS COMPOSITE COLOR (RED + BLUE) | III, IV ARE BLACK<br>DUST IS COMPOSITE COLOR (RED + BLUE) |
| III ▬ IV 430, 440 | III, IV ARE BLUE<br>DUST IS COMPOSITE COLOR (RED + BLUE) | III, IV ARE BLACK<br>DUST IS COMPOSITE COLOR (RED + BLUE) |
| 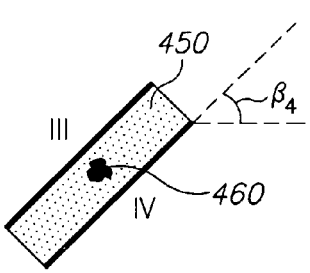 450, 460, $\beta_4$ | FOR $0° \leq |\beta_4| \leq 15°$:<br>III, IV ARE RED<br><br>FOR $15° < |\beta_4| < 75°$:<br>III, IV ARE DARK<br><br>FOR $75° \leq |\beta_4| \leq 90°$:<br>III, IV ARE BLUE<br><br>DUST IS COMPOSITE COLOR (RED + BLUE) | FOR $0° \leq |\beta_4| \leq 15°$:<br>III, IV ARE DARK<br><br>FOR $15° < \beta_4 < 75°$:<br>III, IV ARE RED<br><br>FOR $-75° < |\beta_4| < 15°$:<br>III, IV ARE BLUE<br><br>FOR $75° \leq |\beta_4| \leq 90°$:<br>III, IV ARE DARK |

FIG.6

SYSTEM AND METHOD FOR INSPECTING PATTERNED DEVICES HAVING MICROSCOPIC CONDUCTORS

FIELD OF THE INVENTION

The present invention relates generally to inspection of microscopic features on manufactured objects.

BACKGROUND OF THE INVENTION

Automated Optical Inspection systems for inspecting in-fabrication flat panel displays for defects, including SuperVision™ and InVision™ systems commercially available from Orbotech Ltd. of Yavne, Israel typically include defect classification sub-systems operative to acquire images of suspected defects that are illuminated using polychromatic or monochromatic bright field illumination.

Some automated optical inspection systems for inspecting in-fabrication flat panel displays for defects, for example the Pointer-5000 series of optical testers, also commercially available from Orbotech Ltd, Yavne, Israel, additionally acquire images illuminated with generally monochromatic illumination supplied from locations that are offset from an optical axis.

U.S. Pat. No. 6,947,151 describes a surface state inspecting method and substrate inspecting apparatus employing illumination comprising different colored lights that are irradiated in a plurality of directions having different elevation angles with respect to the inspection object.

The disclosures of all publications mentioned in the specifications, and of the publications cited therein directly or indirectly, are hereby incorporated by reference.

SUMMARY OF THE INVENTION

The present invention seeks to provide an improved system and method for inspecting microscopic features on manufactured objects such as display panels.

One embodiment of the system of the present invention seeks to distinguish between cut and dust defects on an FPD (flat panel display) panel. Both types of defects appear as dark spots in bright-field illumination and appear as bright in dark-field illumination. A preferred embodiment of the present invention achieves the distinction between cut and dust defects by analyzing cut brightness which is very sensitive to the azimuthal direction of illumination whereas dust defects appear bright independent of illumination direction. Preferably, the panel is illuminated simultaneously from a plurality of directions by various colors, thereby to facilitate human visualization and machine analysis of the nature of a seeming defect and keeping inspection time as short as possible. As a result of the multi-directional, multi-spectral illumination of the panel, cut defects have one specific color strongly dependent on their orientation, while dust defects appear as having both colors i.e. having a composite color. The obtained color image may be further analyzed for each color particularly.

A preferred embodiment of the present invention seeks to improve classification of different types of defects observed on an FPD panel and more particularly seeks to distinguish between cut and dust defects. During FPD fabrication, many active layers may be formed on a single glass plate. Ability to identify the defect type may indicate a problem in a production line. The output of the system of the present invention allows the production line to be fixed appropriately, thus increasing production yield.

According to a preferred embodiment of the present invention, a DF (Dark-Field) illumination method is employed, utilizing multi-color illumination apparatus, to distinguish between cut and dust defects. Because of strong light scattering, both types of defects appear as dark spots in conventional bright-field illumination and appear as bright in conventional dark-field illumination. The illumination method is useful in distinguishing between cut and dust defects because cut brightness is very sensitive to azimuthal direction of illumination (azimuthal direction being a direction in an x-y plane) while dust defects appear bright independent of illumination direction.

Preferably, the panel is illuminated simultaneously from a plurality of directions by various colors, different colors being associate with different azimuthal directions, which facilitates human visualization of defect nature, automatic classification and minimization of inspection time. As a result, cut defects have predominant color strongly dependent on orientation, while dust defects appear as a mixture or composite of both or all colors used preferably being such as to be distinguishable and discernable by a human operator or in machine analysis. The resulting color picture can be disassembled into corresponding 1-color figures for further computerized analysis. Since an FPD panel generally comprises known line orientations (e.g. in directions: 0°, 90°, 45° and 135°), the illuminator typically comprises two groups of illuminator units e.g. light emission diodes or optical fibers, arranged in parallel to the known line orientations of the workpiece or panel e.g. along the (0°) and (90°) axes, and the (45°) and (135°) axes, to cover all possible angles.

The method of the present invention is particularly useful for scanning of large cell displays (TV-panels), when comparison between neighboring cells is impossible in which case all information is extracted from the image of single cell.

The system and method of the present invention are particularly useful for automatic optical inspection of flat panel displays.

There is thus provided, in accordance with a preferred embodiment of the present invention, an inspection system operative to inspect patterned devices having microscopic conductors, the system comprising a camera viewing a location of a candidate defect on a patterned substrate, the substrate defining a plane, and acquiring thereat at least one image of the location, the camera defining an optical axis, the at least one image being illuminated by illumination from at least one light source that is offset from said optical axis, the illumination being supplied along at least first and second paths of illumination that are mutually non-parallel in a plane corresponding to the plane, wherein a response to illumination supplied along the first path of illumination is differentiable from a response to illumination supplied along the second path of illumination; and a defect classifier operative to receive the at least one image and to distinguish therewithin a candidate defect caused by a particle foreign to the patterned substrate from other types of candidate defects.

Also provided, in accordance with another preferred embodiment of the present invention, is an inspection method operative to inspect patterned devices having microscopic conductors, the method comprising viewing a location of a candidate defect on a patterned substrate, the substrate defining a plane, and acquiring thereat at least one image of the location, the camera defining an optical axis; illuminating the at least one image with illumination from at least one light source that is offset from the optical axis, the illumination being supplied along at least first and second paths of illumination that are mutually non-parallel in a plane corresponding to the plane, wherein a response to illumination supplied along the first path of illumination is differentiable from a response to illumination supplied along the second path of illumination; and analyzing the at least one image to distinguish therewithin a candidate defect caused by a particle foreign to the patterned substrate from other types of candidate defects.

Also provided, in accordance with yet another preferred embodiment of the present invention, is an inspection system operative to inspect patterned devices having microscopic conductors, the system comprising a camera viewing a location of a candidate defect on a patterned substrate, the substrate defining a plane, and acquiring thereat at least one image of the location, the camera defining an optical axis, the at least one image being illuminated by illumination from at least one light source that is offset from the optical axis, the illumination being supplied along at least first and second paths of illumination that are mutually non-parallel in a plane corresponding to the plane, wherein a response to illumination supplied along the first path of illumination is differentiable from a response to illumination supplied along the second path of illumination; and a defect classifier operative to use the at least one image to distinguish a defect caused by a cut in an at least partially conductive area of the patterned substrate, from at least one other type of defect.

Also provided, in accordance with another preferred embodiment of the present invention, is an automatic inspection system operative to inspect electro-optical devices having microscopic conductors, the system comprising a defect classifier operative to acquire a plurality of dark field illuminated images of a corresponding plurality of defect locations and to generate a corresponding plurality of outputs corresponding thereto which distinguish directional defects such as cuts from non-directional defects such as particles. Preferably, multiple dark field illuminations are employed.

Further in accordance with another preferred embodiment of the present invention, the plurality of outputs comprise dark field illuminated images.

Still further in accordance with another preferred embodiment of the present invention, the plurality of outputs comprises a respective plurality of categorizations of the respective plurality of defect locations, at least one of the categorizations being a directional defect categorization and at least another one of the categorizations being a non-directional defect categorization.

Further in accordance with another preferred embodiment of the present invention, the images are illuminated multi-directionally.

Still further in accordance with another preferred embodiment of the present invention, the images are illuminated multi-spectrally.

Still further in accordance with another preferred embodiment of the present invention, the images are illuminated by directional illumination having the same optical characteristics but from different directions separated by time.

Also provided, in accordance with another preferred embodiment of the present invention, is a method for automated optical inspection of manufactured objects having microscopic features, the method comprising using multi-spectral multi-angular dark field imagery for verification of defects in a manufactured object.

Further in accordance with another preferred embodiment of the present invention, the manufactured object comprises a flat panel display.

Also provided, in accordance with another preferred embodiment of the present invention, is an automatic inspection system operative to inspect manufactured objects having microscopic features, the system comprising an optical head operative to image at least a portion of a manufactured object having microscopic features and a relative motion provider operative to provide relative motion between the manufactured objects to be inspected and the optical head, wherein the optical head comprises a multidirectional illuminator operative to provide illumination from a plurality of directions, the multidirectional illuminator comprising a plurality of different colored illumination sources providing illumination from a respective plurality of directions.

Also provided, in accordance with another preferred embodiment of the present invention, is system for inspecting defects of more than one types, wherein a first of the defect types is configured to have edges lying along a known edge axis and a second of the defect types is not configured to have edges along the known edge axis, the system comprising an illuminator operative to direct edge-detecting illumination at an edge-detecting angle to the known edge axis.

Further in accordance with another preferred embodiment of the present invention, the first defect type comprises a cut and the second defect type comprises a dust particle.

Still further in accordance with another preferred embodiment of the present invention, the edge-detecting illumination comprises DF illumination.

Additionally in accordance with another preferred embodiment of the present invention, the edge-detecting angle comprises a 90 degree angle.

Further in accordance with another preferred embodiment of the present invention, the illuminator is operative to direct edge-detecting illumination at edge-detecting angles to a plurality of known edge axes.

Still further in accordance with another preferred embodiment of the present invention, the illumination directed at the plurality of known edge axes is of different colors thereby to enable illumination directed at different ones from among the plurality of known edge axes.

Also provided, in accordance with another preferred embodiment of the present invention, is a system for inspecting patterned panels for defects, the system comprising an automatic optical inspection sub-system inspecting a pattern formed on a flat panel, the pattern having edges, and outputting indications of candidate defect locations thereon, and a defect verifier including a camera, an illuminator and an image processor, the illuminator providing, for a candidate defect at a candidate defect location, an edge detecting illumination impinging on the candidate defect at a predetermined edge detecting angle relative to the edge.

BRIEF DESCRIPTION OF THE DRAWINGS

Preferred embodiments of the present invention are illustrated in the following drawings:

FIGS. 3A-3C are side, end and bottom views, respectively, of the illuminator of FIG. 2.

FIG. 5A is a table showing the appearance of several elongate elements having various orientations, with or without perpendicular cuts, under the first and second illumination modes of FIGS. 1A and 1B respectively.

FIG. 5B is a table showing the appearance of horizontal and vertical elongate elements having diagonal cuts, under the first and second illumination modes of FIGS. 1A and 1B respectively.

FIG. 6 is a table showing the appearance of several types of dust-electrical conductor configurations under the first and second illumination modes of FIGS. 1A and 1B respectively.

DETAILED DESCRIPTION OF PREFERRED EMBODIMENTS

Figure 1A:
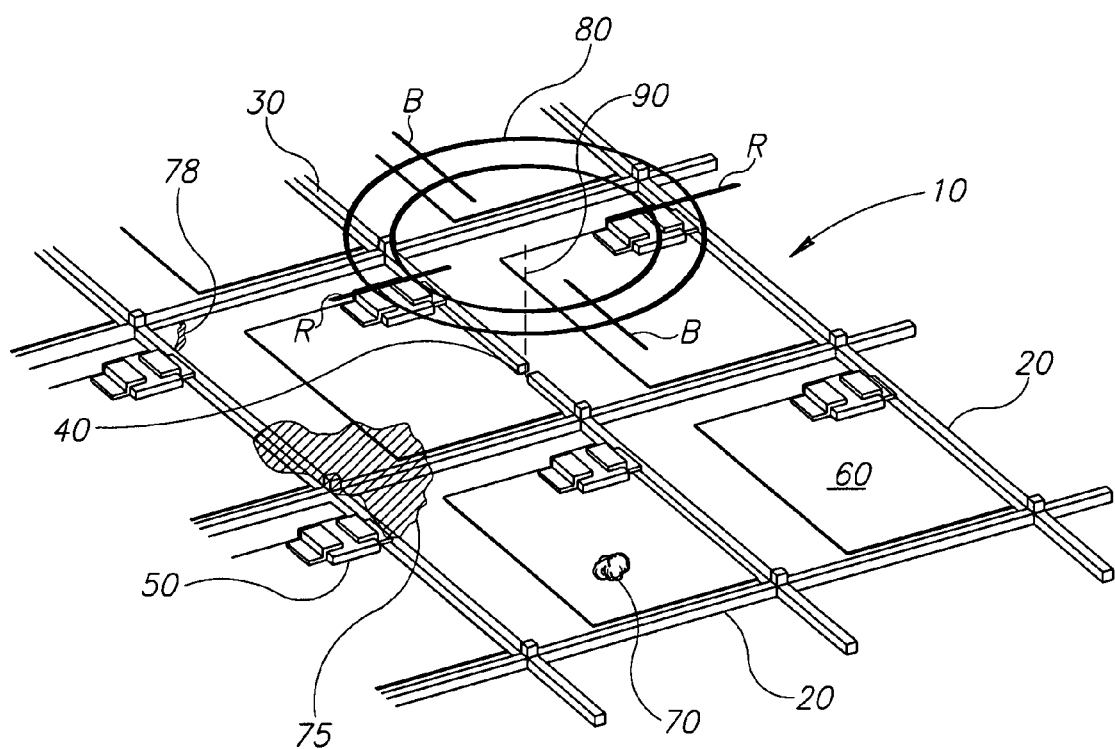
FIG. 1A is a pictorial illustration of a portion of a display panel including a plurality of elongate elements such as electrical conductors and showing various representative of defect types, wherein the display panel is being inspected using a multi-color, multi-directional inspection process operating in a first illumination mode.

FIG. 1A is a simplified pictorial illustration of a portion of a display panel 10 including a plurality of elongate elements 20, such as electrical conductors, one of which 30 has a cut defect at defect location 40, and also includes transistors 50, electrodes 60, and other electrical components. Other defects that may appear on a display panel 10 include foreign particles 70, such as dust, which may be found on an outer surface of panel 10 or buried beneath a coating such as a photo resist (not seen), chemical residues 75, and shorts 78 forming an undesired electrical connection between two conductors 20. The display panel 10 requires inspection at defect location 40, for example in order to classify the type of defect thereat, for example as a cut, particle, short or other class of defect. The presence of a candidate defect location may be determined by initial automated inspection, for example using SuperVision™ or InVision™ automated optical inspection equipment commercially available from Orbotech Ltd. of Yavne, Israel, although this need not be the case.

In accordance with an embodiment of the invention, a multi-color, multi-directional inspection device providing directionally specific illumination, schematically represented by bull's-eye 80 centered on an optical axis 90, is operating in a first illumination mode according to an embodiment of the present invention. As shown, the first illumination mode comprises direction-specific illumination offset from the optical axis, and supplied along non-parallel axes, generally orthogonal axes being shown, which are substantially parallel to the conductors 20 on the panel 10 being inspected. The first illumination mode may for example comprise illumination of a first wavelength such as blue, schematically represented as "B", directed from two opposite directions and illumination of a second wavelength such as red, schematically represented as "R", directed from a further two opposite directions which are non-parallel relative to the first two opposite directions. When viewed along axis 90, a response at a location illuminated to illumination in the first wavelength is distinguishable from illumination in the second wavelength.

Figure 1B:
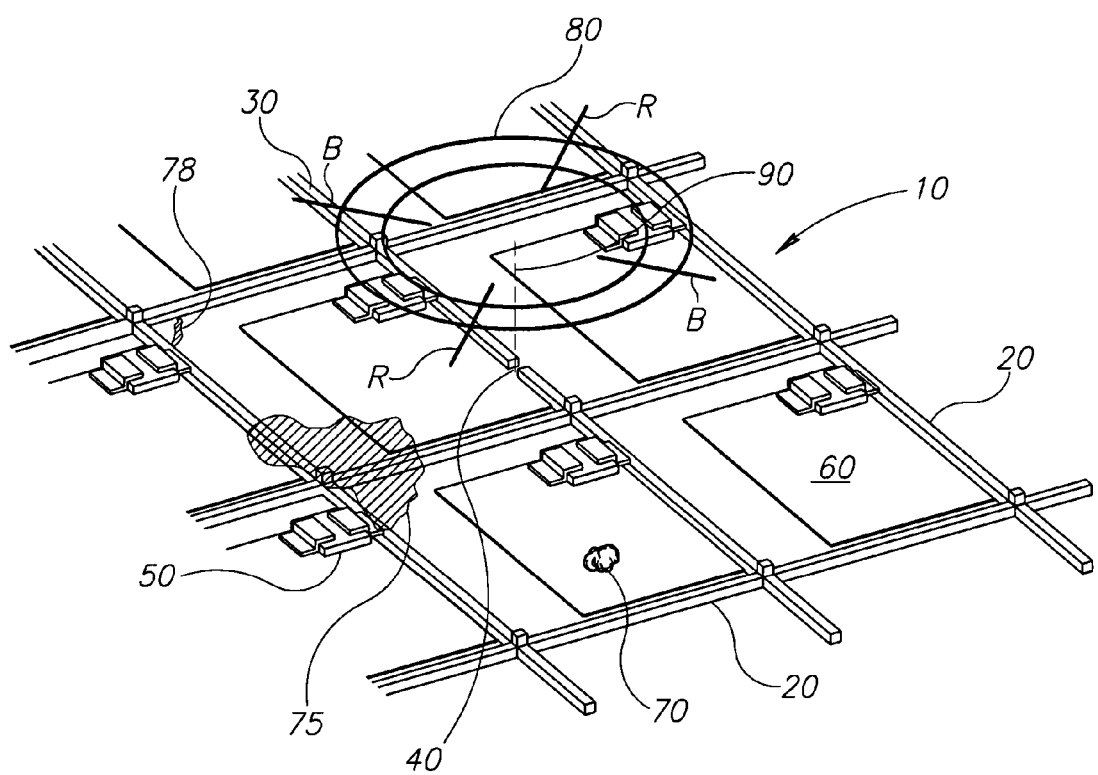
FIG. 1B is a pictorial illustration of the display panel of FIG. 1A, wherein the display panel is being inspected using the multi-color, multi-directional inspection process of FIG. 1A which is now operating in a second illumination mode.

FIG. 1B is a pictorial illustration of the display panel seen in FIG. 1A, wherein the display panel is being inspected using the multi-color, multi-directional inspection device of FIG. 1A which is now operating in a second illumination mode. In the second illumination mode of FIG. 1B, illumination also comprises direction-specific illumination offset from the optical axis, and supplied along non-parallel axes, generally orthogonal axes being shown, which are preferably angled with respect to the conductors 20 on the panel 10 being inspected. The second illumination mode may for example comprise illumination of a first wavelength such as blue, schematically represented as "B", directed from two opposite directions which are separated from the first pair of illumination directions used in the first illumination mode, by 45 degrees in the plane of panel 10 being inspected, and illumination of a second wavelength such as red, schematically represented as "R", directed from a further two opposite directions which are perpendicular to the first two opposite directions used by the second illumination mode. Although Red and Blue illumination are shown, it is noted that other forms of suitable illumination having mutually distinguishable responses when viewing a location on panel 10 may be employed. Such other forms of illumination include, for example illumination in other spectra, illumination distinguishable by polarization, pulsed illumination provided at different pulse frequencies, or illumination distinguishable by other suitable characteristic.

Figure 2:
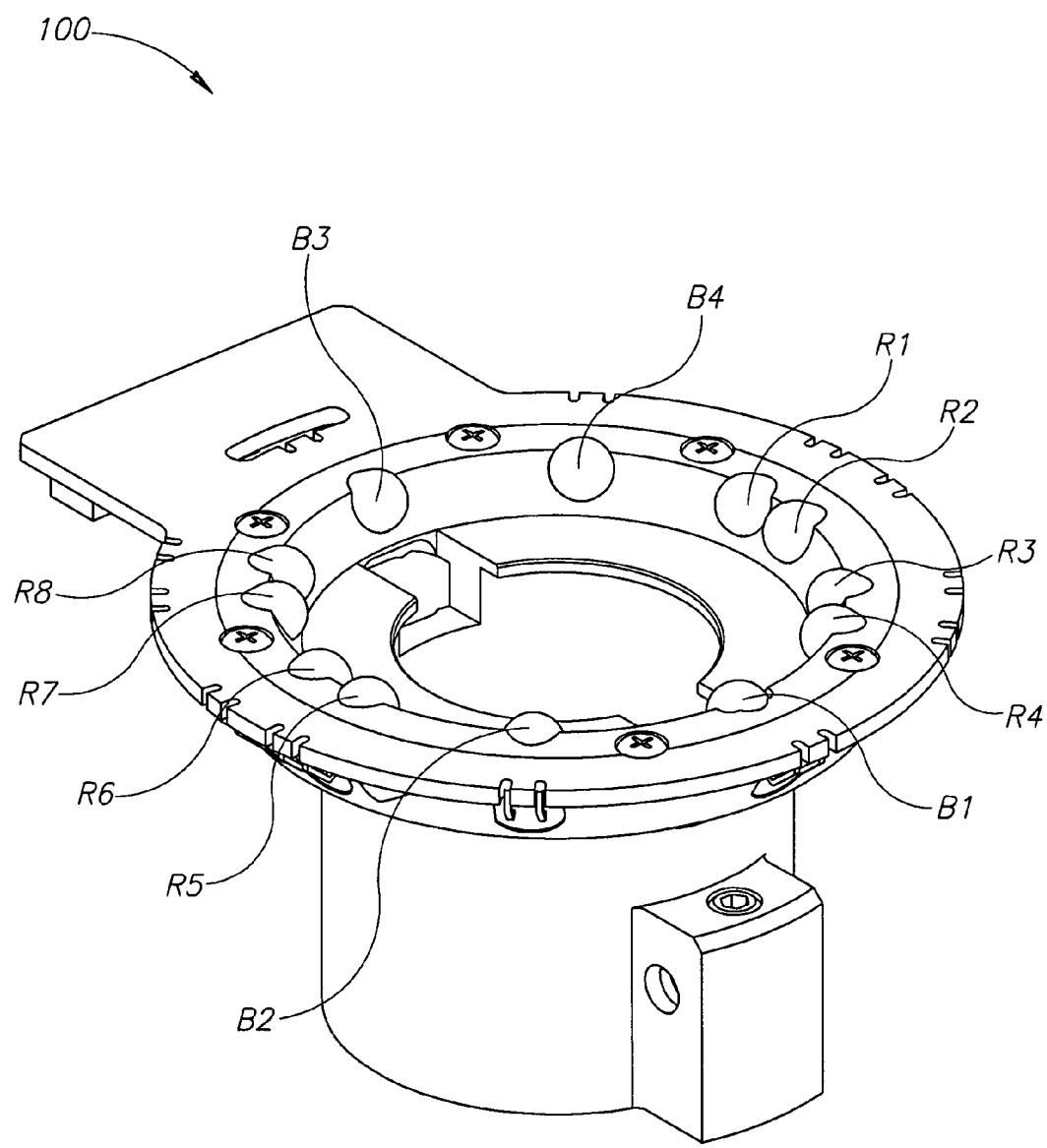
FIG. 2 is an illuminator constructed and operative in accordance with a preferred embodiment of the present invention which provides illumination in the two selectable illumination modes illustrated in FIGS. 1A and 1B respectively.

FIG. 2 is an illumination sleeve 100 constructed and operative in accordance with an embodiment of the present invention to provide illumination in the two selectable illumination modes illustrated in FIGS. 1A and 1B respectively. The illumination sleeve 100 comprises a plurality of illuminators such as selectably operable light-emitting diodes R1-R8 and B1-B4 which provide the first and second illumination modes of FIGS. 1A and 1B. The diodes preferably comprise sets of one or more diodes at each of a plurality of directions, such as the 8 azimuthal orientations of 0, 45, 90, 135, 180, 225, 270 and 315 degrees respectively. Alternatively, other groups of angles may be employed which typically include at least one angle capable of illuminating each of the expected directions defined by the expected directional features such as edges. Any suitable LEDs may be employed such as the following LEDs commercially available from Agilent Technologies (Blue: Cat. No. HLMP CB-18UVA00; Red Cat. No. HLMP EG08-Y2000).

Typically, illuminator sets of one color such as blue are positioned opposite each other to define a first illumination path whereas illuminator sets of a second color such as red are positioned opposite each other to define a second illumination path not parallel to the first illumination path. Each set of red diodes typically comprises two diodes whereas each set of blue diodes typically comprises only a single diode since in an embodiment two red diodes are typically required to achieve sufficient brightness. Subject to improvements in diode technology, and application requirements with respect to illumination intensity, the same number of diodes for each color may be suitable. In the illustrated embodiment, a pair of red diodes (R1 and R2; R3 and R4; R5 and R6; and R7 and R8) are centered at each of the 0, 45, 180 and 225 degree angular positions respectively whereas a single blue diode (B1, B2, B3 and B4) is located at each of the 90, 135, 270 and 315 degrees respectively.

FIGS. 3A-3C are side, end and bottom views, respectively, of the illuminator sleeve 100 of FIG. 2. It is noted that in accordance with an embodiment of the invention, illuminator sleeve 100 is dimensioned to slide over the objective lens of a video microscope, to provide multi-colored direction specific illumination as described hereinabove.

Figure 4A:
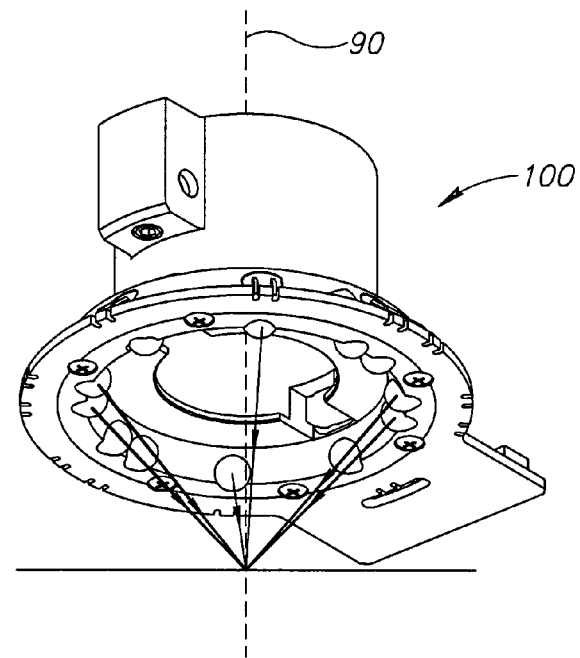
FIG. 4A is a pictorial diagram showing the illuminator of FIGS. 2-3C operative in its first illumination mode and showing illumination rays.
Figure 4B:
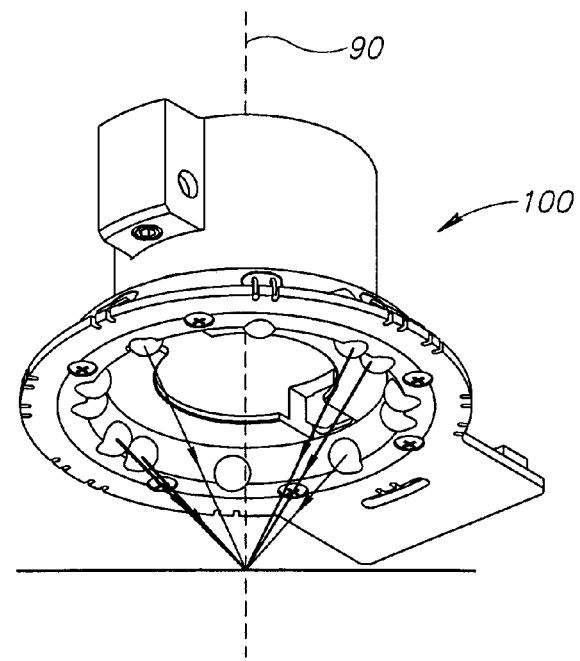
FIG. 4B is a pictorial diagram showing the illuminator of FIGS. 2-3C operative in its second illumination mode and showing illumination rays.

FIG. 4A is a pictorial ray diagram showing illuminator sleeve 100 of FIGS. 2-3C operative in its first illumination mode. FIG. 4B is a pictorial ray diagram showing the illuminator of FIGS. 2-3C operative in its second illumination mode. Heavy arrows show rays of a first color such as red whereas non-heavy (thin) arrows show rays of a second color such as blue, and the broken line shows an optical axis 90.

Figure 4C:
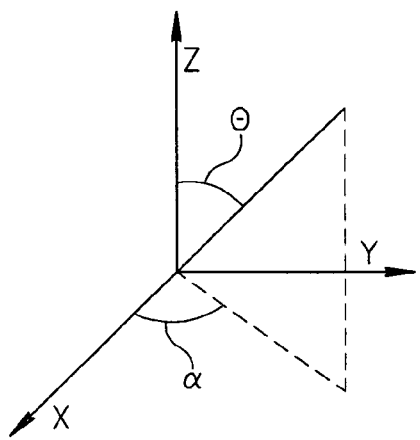
FIG. 4C is a simplified pictorial illustration of an angular orientation for illumination offset from the optical axis provided by the illuminator of FIGS. 2-3C.

In an embodiment of the invention, the angle of elevation $\theta$ at which illumination is supplied is selected to optimize the respective brightness of particle and cut defects when imaged by a camera viewing the location of a candidate defect. Defining dark field illumination angles, $\theta$ and $\alpha$, are shown in FIG. 4C. Angle $\theta$ is measured from the vertical axis z (the axis normal to the x-y plane of the panel), to the illumination ray which is indicated. Angle $\alpha$ is an angle corresponding to a rotational, or azimuthal, orientation in the x-y plane of a panel to be inspected of the illumination ray.

Typically, in an in-fabrication flat panel display elongate elements such as conductors have distinguishable edges and are arranged in rows and columns to define a matrix. Other features and defects such as cuts, scratches and shorts also have distinguishable edges. Angle of elevation $\theta$ is selected to avoid over exposure of edges relative to other detectable features such as particles, and to optimize exposure uniformity, to the extent possible, among edges and particles. Angle $\alpha$ may be selected so that each of the respective first and second axes of illumination is generally perpendicular to one of the conductor directions. In an embodiment of the invention, the orientation of conductors at a given location is not known, or may change within an image frame. Accordingly, first and second illumination modes described above with respect to FIGS. 1A and 1B are provided.

Figure 4D:
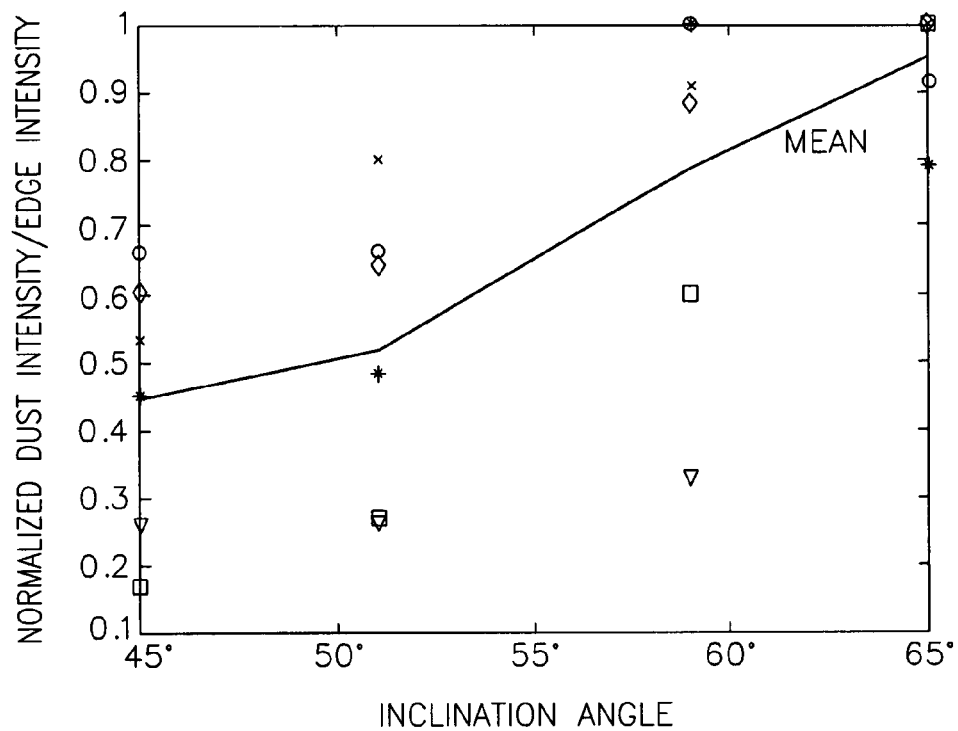
FIG. 4D is a graph plotting a ratio between an intensity of response to illumination for dust relative to edges brightness as a function of an angle between an incident illumination beam and an optical axis.

FIG. 4D is a graph useful as an aid in selecting an angle of elevation $\theta$. FIG. 4D plots for selected particles the ratio of the light intensity of the selected illuminated particles relative to the light intensity of illuminated conductor edges on a panel, as a function of the angle of elevation (or inclination) $\theta$ of the illumination. Thus for each selected particle the intensity of a response to illumination is measured and divided by the intensity of a response to illumination for edges, which is generally constant. The results are then normalized, and the normalized result is plotted. Curve 110 connects the mean average for the results for each particle at a given angle $\theta$ of elevation showing the light intensity of an illuminated particle relative to an illuminated edge.

As seen in the graph of FIG. 4D, as the angle of elevation $\theta$ approaches 65°, the average normalized ratio of the intensity of a response to illumination of particles relative to the intensity of a response to illumination of edges approaches 1, meaning that on average the relative intensities for particles and edges are nearly equal. Although as seen in FIG. 4D, an angle of elevation $\theta$ near 65° would be desirable, because of near uniformity in illumination intensity among particles and edges. In an embodiment of the invention, due to physical limitations, for example limits on the working distance of an objective lens, the angle of elevation $\theta$ is selected to be about $\theta=60°$.

Figure 4E:
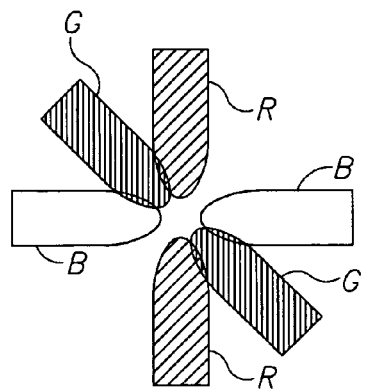
FIG. 4E is a simplified pictorial illustration of a first multi-directional illumination mode useful in differentiating directional defects from non-directional defects, in which three colors are used.
Figure 4F:
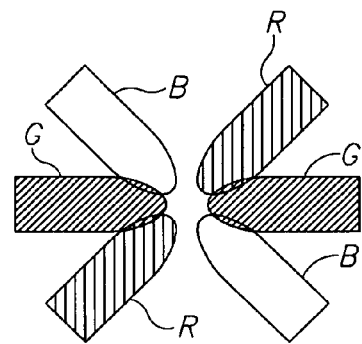
FIG. 4F is a simplified pictorial illustration of a second multi-directional illumination mode useful in differentiating directional defects from non-directional defects, in which three colors are used.

It is appreciated that provision of two illumination modes, specifically, as shown in FIGS. 4A and 4B, is not intended to be limiting. Alternatively, more or less than two illumination modes may be employed to distinguish directional local effects such as cuts from non-directional local effects such as foreign particles. Also, provision of two colors of illumination is not intended to be limiting. Alternatively, a single color, or polychromatic illumination, may be used, in which case more images are typically acquired, for example each of the images being distinguishable in a time domain, or more than two colors may be employed as shown, by way of example, in FIGS. 4E and 4F, or images that are directionally illuminated by illumination that is distinguishable by some other characteristic such as polarization or pulse frequency. Both of the images of FIGS. 4E and 4F may be acquired and compared, or alternatively, only one of these three-colored images may be acquired.

Specifically, whereas in the embodiment of FIGS. 4A and 4B there are two groups of illuminators: {Blue: 0°, 180°; Red: 90°, 270°} and {Blue: 135°, 315°; Red: 45°, 225°}, alternatively, other orientations of illuminators may be employed. For example: in each illumination mode, a single illumination direction may be used for each color instead of utilizing two different illumination directions (separated, in the embodiment of FIGS. 4A-4B, by 180 degrees) for each color. The arrangement of direction specific illumination thus accommodates different angles of conductors on a panel to be inspected.

Figure 4G:
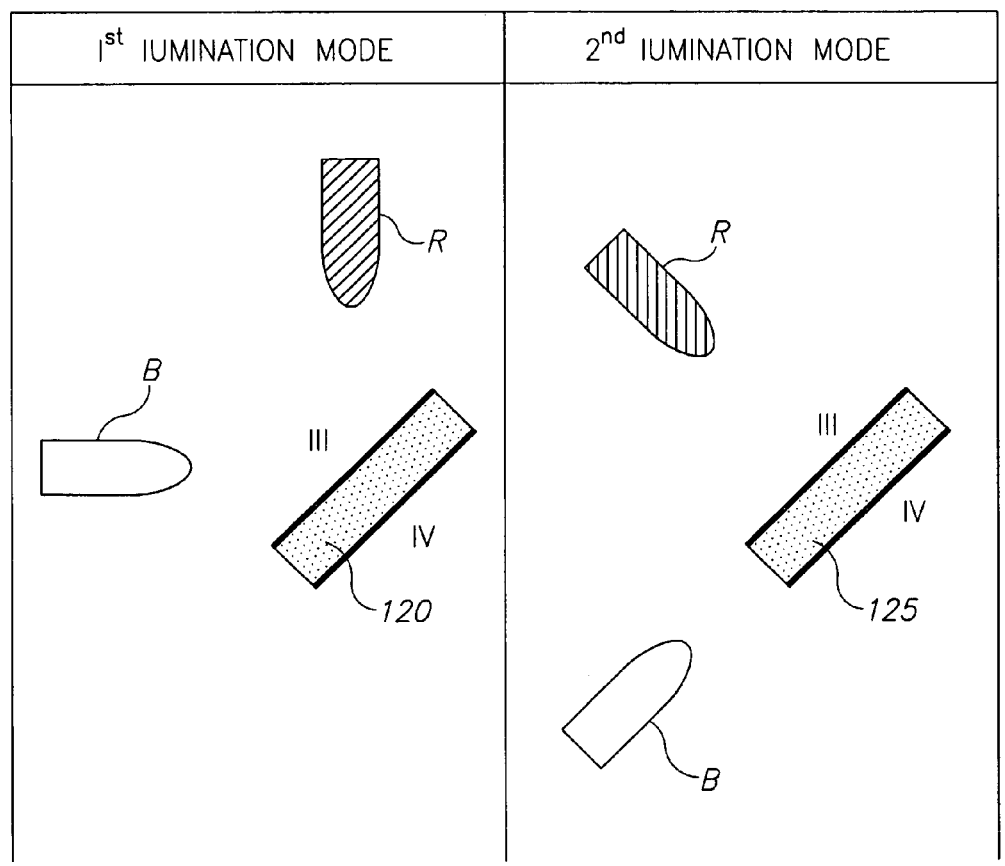
FIG. 4G is a simplified pictorial illustration of a pair of illumination modes useful for differentiating directional defects from non-directional defects by acquiring and comparing two images of each candidate defect, under the two illustrated illumination modes respectively.

In embodiment seen in FIG. 4G, the illumination of a conductor (or other elongate element, the term "conductor" in this description being used merely by way of example) typically is not homogeneous from opposite directions. Moreover, a conductor edge closer to the source of illumination may be seen to be brighter than the conductor edge further from the source of illumination, provided that it is generally perpendicular to a rotational angle $\alpha$ of illumination. If the conductor is illuminated by illumination from an angle $\alpha$ that is not nearly perpendicular to the edge, it may appear dark and may not be seen or detected. It is noted that from the perspective of image analysis, the non-visibility of properly formed edges properly extending in a known direction is desirable; one result is to highlight in the image various anomalies such as foreign particles and defects in the formation of conductors such as cuts, scratches, extraneous metallic formations that may result short circuits and the like.

FIG. 4G shows the direction specific nature of distinguishable illumination. For example, for the conductor 120 in FIG. 4G, in the first mode of illumination edges III and IV will appear dark in response to both red and blue illumination, as shown, in an image acquired along an optical axis normal to the substrate on which the conductors are located.

In the second mode of illumination of FIG. 4G, in an image acquired along an optical axis normal to the substrate on which the conductors are located, edges III and IV of conductor 125 will be seen in response to red illumination, as shown. However edge III will appear somewhat stronger (i.e. more intense) than edge IV. Conversely, both of edges III and IV will appear dark in response to blue illumination, as shown and neither will be seen. In this manner, by changing the direction of illumination, various known features in a patterned substrate, for example conductor edges, may be made selectably visible or hidden in acquired images, as desired.

In the illustrated embodiment, the angle between each two neighboring light sources is 90 degrees (in each illumination mode). This structure is suitable for analyses of FPD panels in which conductor lines are arranged in generally uniform rows and columns in which conductor lines predominately occur at angles 0°, ±45°, 90°, and 135°. However, according to an alternative embodiment of the present invention, angles between light sources may be changed as necessitated by a given inspection application.

FIGS. 5A and 5B are tables showing the appearance of several types of cut defect-elongate element configurations under the first and second illumination modes of FIGS. 1A and 1B respectively. The left-hand column, 200, of the table of FIG. 5A illustrates a number of microscopic features such as a segment 210 of a horizontally disposed electrical conductor (the term "conductor" being used herein as an example of an elongate element), a segment 220 of a vertically disposed electrical conductor, a segment 230 of a horizontally disposed electrical conductor in which there is a perpendicularly disposed cut 240, a segment 250 of a vertically disposed electrical conductor in which there is a perpendicularly disposed cut 260, and a segment 270 of a diagonally disposed electrical conductor in which there is a perpendicularly disposed cut 280.

The left-hand column, 200, of the table of FIG. 5B illustrates a number of microscopic features such as a segment 292 of a horizontally disposed electrical conductor in which there is a diagonally disposed cut 294, and a segment 296 of a vertically disposed electrical conductor in which there is a diagonally disposed cut 298.

The middle column 310 of the table in FIGS. 5A and 5B describes the appearance of the various features in column 200, under a first illumination mode 320 illustrated schematically, in which blue illumination is provided from both directions along the horizontal axis and red illumination is provided from both directions along the vertical axis. The right-side column 330 of the table of FIGS. 5A-5B describes the appearance of the various features in column 200, under a second dark-field illumination mode 340 illustrated schematically, in which blue illumination is provided from both directions along the 135-315 degree axis and red illumination is provided from both directions along the 45-225 degree axis. As shown, edges, such as conductor edges or other elongate element edges marked with solid lines or cut edges marked with dots, which are perpendicular to the direction of an illumination of a given color, will appear in that color. Edges, such as elongate element edges marked with solid lines or cut edges marked with dots, which are angled vis a vis the direction of the illumination, e.g. at a 45 degree angle, appear dark. Other than the feature portions whose colors are specifically indicated in columns 310 and 330, the feature appears dark.

FIG. 6 is a table showing, in columns 310 and 330, the appearance of several types of foreign particle-electrical conductor configurations under the first and second illumination modes of FIGS. 1A and 1B respectively. The first feature of FIG. 6 is a horizontal conductor 400 on which is resting a foreign particle 420, such as dust. The second feature of FIG. 6 is a vertical conductor 430 on which a dust particle 440 is resting and the third feature of FIG. 6 is a diagonal conductor 450 on which a dust particle 460 is resting. Foreign particles 420, 440 and 460 may be entirely on the surface of a panel to be inspected or entrapped underneath a coating such as a photo resist coating. As shown, due to the plethora of irregular edges on dust particles, the foreign particles scatter illumination received from a variety of directions and when illuminated by different colored direction specific illumination, typically are seen in a composite color such as purple (if the direction specific colors are red and blue), in both illumination modes. This allows them to be clearly distinguished from the various cuts shown in FIG. 5A-5B, which typically are seen in illumination supplied in specific direction, but not in illumination supplied in other directions.

It is appreciated that the endpoints of the angle ranges given in FIGS. 5A, 5B and 6, columns 310 and 33, for the orientations of segments 270 and 450 and of cuts 292 and 298 are exemplary for a specific application and are not appropriate for all applications. The information in columns 310 and 330 for these segments is correct generally for small, medium and large angles, however the precise cut-off points of the small, medium and large angle ranges need not be 15 and 75 degrees as shown and are preferably determined empirically for each application.

It is appreciated that the tables of FIGS. 5A, 5B and 6 may be employed by an operator or a suitable image processing system to categorize defects or candidate defects, in an in-line or off-line automated inspection system, as being due to dust or alternatively as being due to a cut having any of various orientations, by inspecting image pairs of the defects or candidate defects, acquired using the illumination modes 330 and 340 respectively.

The following defect categorization scheme may be employed to classify defects, in a device including red and blue directionally specific illumination in accordance with the embodiment of FIGS. 1A and 1B, for example:

If conductor edges are red in the first illumination mode and dark in the second illumination mode, and the defect is blue in the first illumination mode and dark in the second illumination mode, the defect is a cut in a horizontal conductor.

If conductor edges are red in the first illumination mode and dark in the second illumination mode, and the defect is dark in the first illumination mode and blue in the second illumination mode, the defect is a cut in a horizontal conductor.

If conductor edges are red in the first illumination mode and dark in the second illumination mode, and the defect is red in the first illumination mode and dark in the second illumination mode, the defect is a cut in a horizontal conductor.

If conductor edges are blue in the first illumination mode and dark in the second illumination mode, and the defect is red in the first illumination mode and dark in the second illumination mode, the defect is a cut in a vertical conductor.

If conductor edges are blue in the first illumination mode and dark in the second illumination mode, and the defect is dark in the first illumination mode and red in the second illumination mode, the defect is a cut (feature 298, positive inclination angle).

If conductor edges are blue in the first illumination mode and dark in the second illumination mode, and the defect is dark in the first illumination mode and blue in the second illumination mode, the defect is a cut (feature 298, negative inclination angle).

If conductor edges are blue in the first illumination mode and dark in the second illumination mode, and the defect is blue in the first illumination mode and dark in the second illumination mode, the defect is a cut.

Similarly, if conductor edges are dark in the first illumination mode and red in the second illumination mode, the defect is observed along a forward diagonal conductor, and a suitable classification may be devised based on the analysis of defective segments in the tables of FIGS. 5 and 6. However, if conductor edges are dark in the first illumination mode and blue in the second illumination mode, the defect is observed along a backward diagonal conductor, and a suitable classification may be devised based on the analysis of defective segments in the tables of FIGS. 5 and 6.

If the defect is a composite color (includes both red and blue illumination components arranged non-uniformly) both in the first illumination mode and in the second illumination mode, the defect is typically a light diffusive particle irrespective of the color or direction of the conductor edges.

It is noted that by the use of different colors directional information becomes available in a single image. Similarly, directional information would be available in a sequence of time separated images illuminated with directionally specific illumination. However, by the use of directionally specific colored illumination, various difficulties related to registration of information and correlation between defects seen in different time separate images of the same location are obviated. While reference is made here to different colors, illumination having another differentiable optical characteristic, for example polarization or a pulse frequency, may be employed.

Figure 7A:
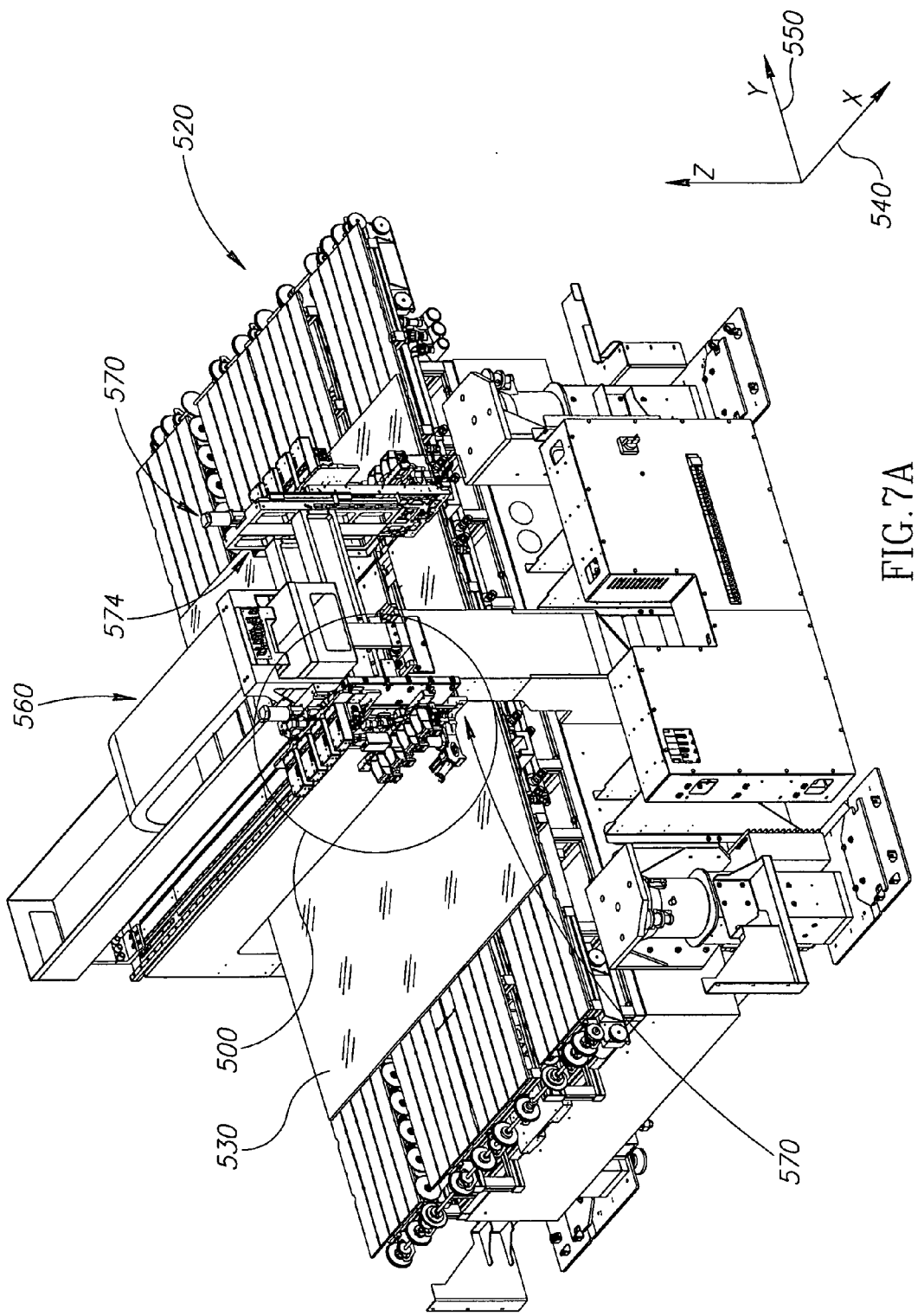
FIG. 7A is a perspective view of a workpiece mounted on a scanning and video verification system constructed and operative in accordance with a preferred embodiment of the present invention which incorporates the illuminator of FIG. 2.
Figure 7B:
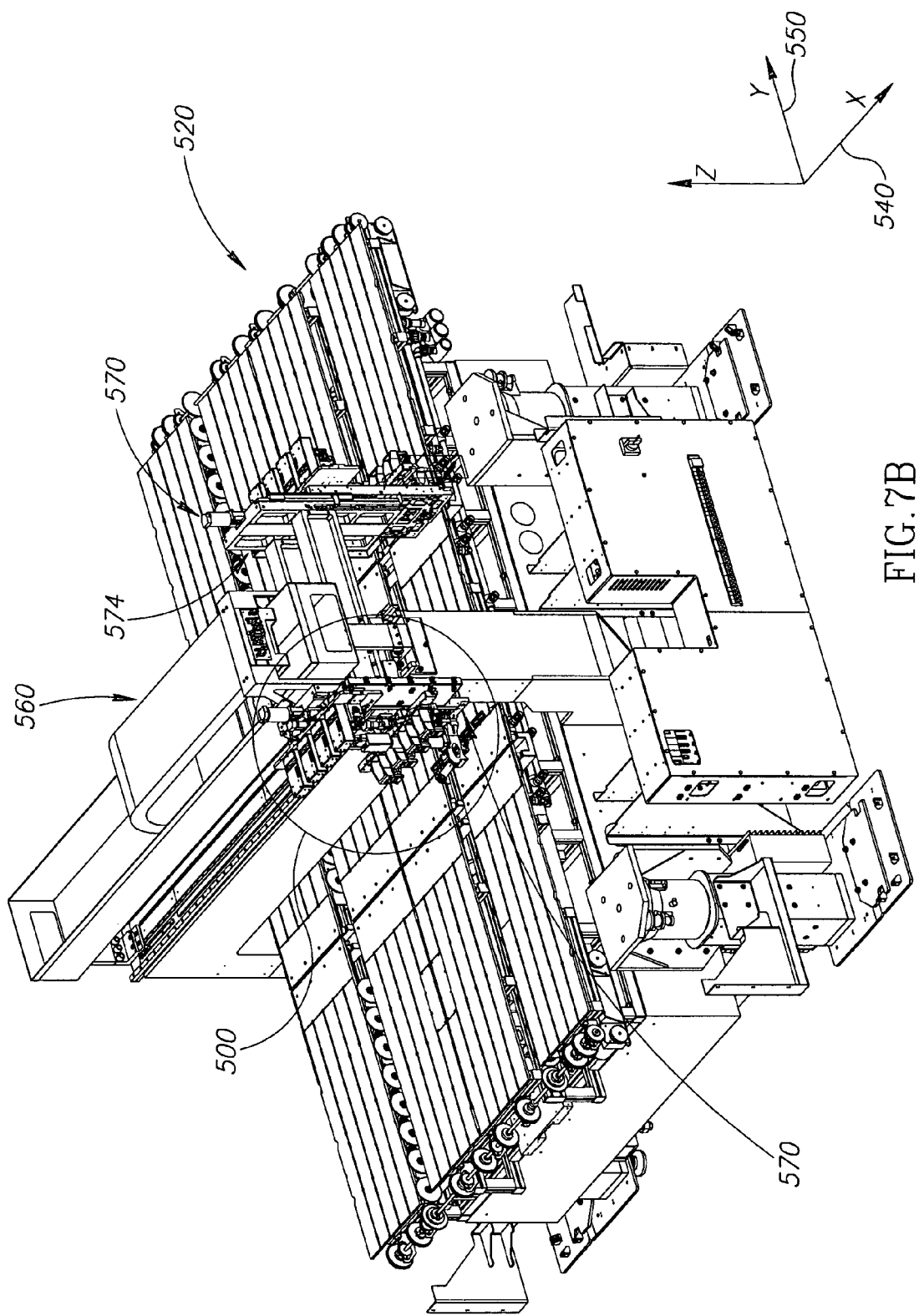
FIG. 7B is a perspective view of the scanning and video verification system of FIG. 7A, the workpiece having been removed.
Figure 8:
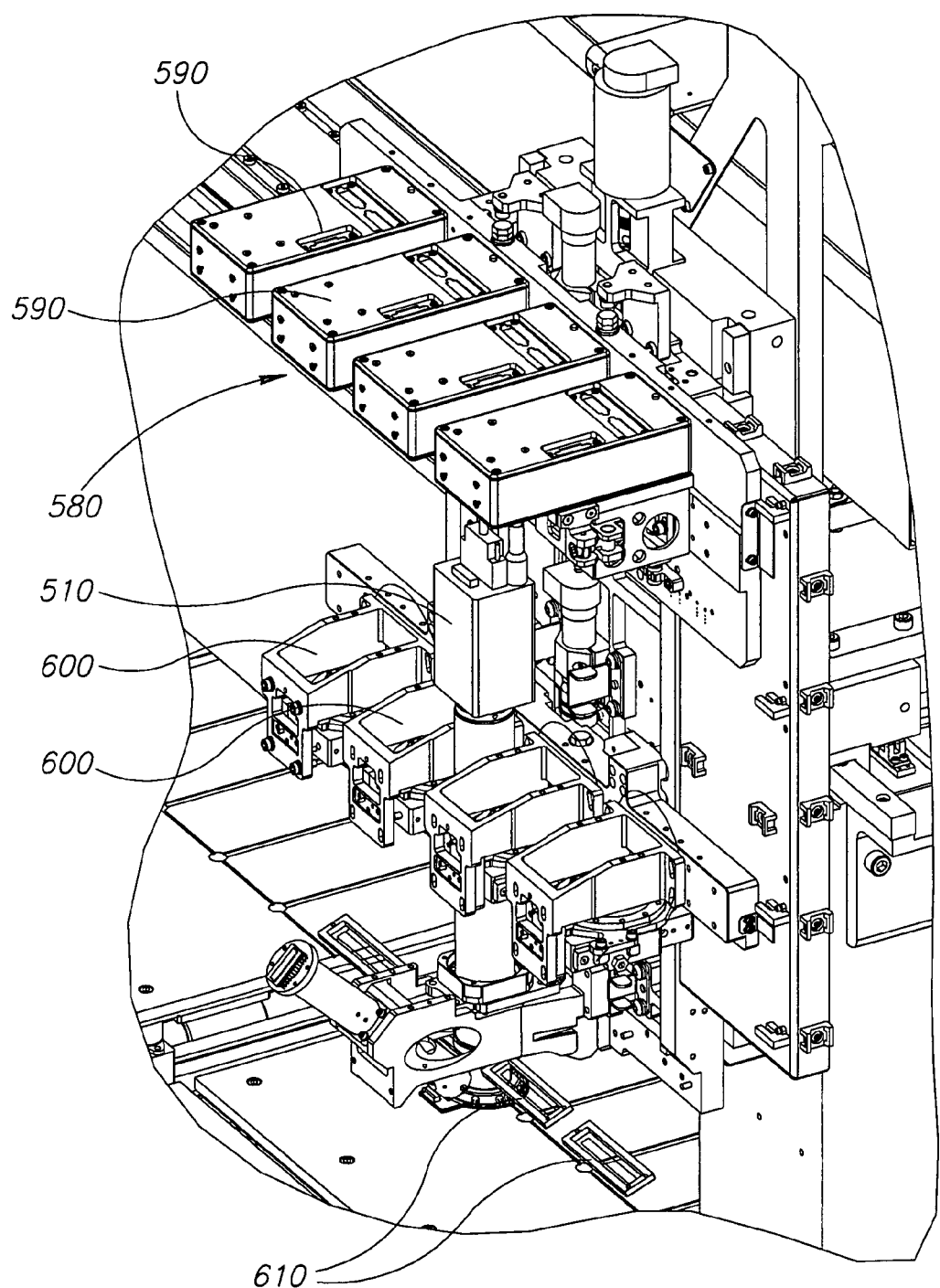
FIG. 8 is an enlarged view of the optical head of FIGS. 7A-7B in which various covers have been removed.
Figure 9:
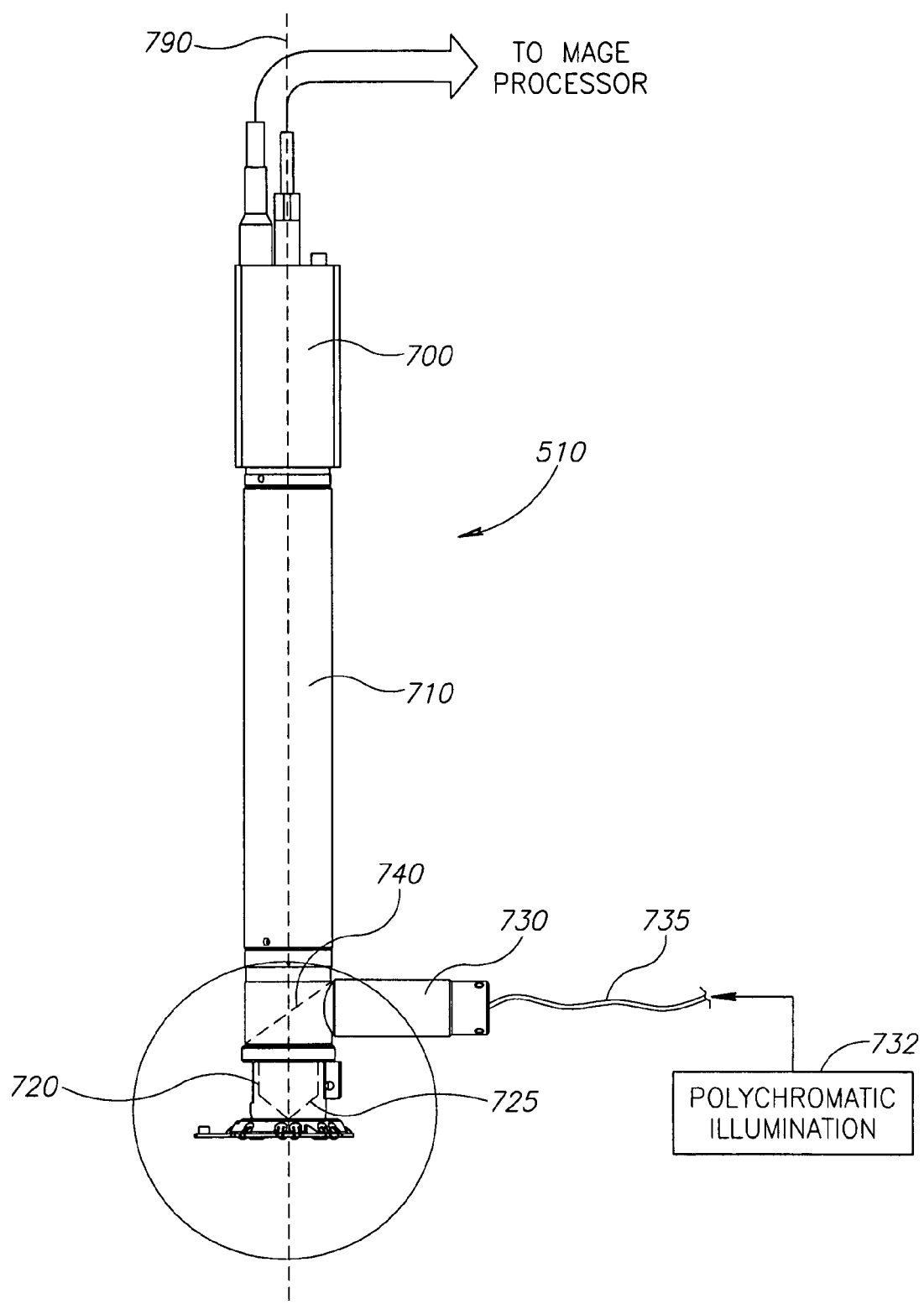
FIG. 9 is a side view illustration of the verification camera subsystem of FIGS. 7A-7B.

FIGS. 7A-7B are perspective views of a scanning automated optical inspection and video verification system constructed and operative in accordance with a preferred embodiment of the present invention which incorporates the illuminator of FIG. 2, from which holders and covers have generally been removed. FIG. 8 is an enlarged view of one of the two optical heads of FIG. 7, as referenced by bubble 500. FIG. 9 is a side view illustration of the defect verification camera subsystem 510 of the optical head, as best seen in FIG. 8. It is appreciated that the apparatus of FIGS. 7A-9 may generally be similar to the SuperVision™ automated optical inspection systems commercially available from Orbotech Ltd., Yavne, Israel, except as specifically described below.

The scanning and video verification system of FIGS. 7A-7B generally includes a work-table such as an air float table 520 on which a workpiece 530 is mounted for motion along the y axes 550. A levitating conveyor suitable for use in the automated optical inspection and video verification system of FIGS. 7A-7B is described in greater detail in U.S. Pat. No. 6,810,297, the disclosure of which is incorporated herein by reference in its entirety. In FIG. 7B, the workpiece 530 has been removed. An optical bridge 560 supports one or more optical heads 570 (two optical heads, in the illustrated embodiment, one supported directly by the optical bridge 560 and another supported by a sub-bridge 574). Each optical head 570 is mounted for motion along the x axis 540 and comprises an array 580 of camera subunits (four such subunits in the illustrated embodiment). Each camera subunit comprises a camera such as a scan camera 590, scan camera optics 600, and a scan illuminator 610. One or more of the optical heads 570 also comprise one or more defect verification camera subunits 510 (one such subunit, in the illustrated embodiment) as described above with reference to FIG. 9.

The defect verification camera subsystem 510, seen in more detail in FIG. 9, is typically configured as a high resolution video microscope and typically comprises a camera 700 such as a video camera (e.g. a 3 CCD camera, available from JAI Corporation of Denmark), a tube lens 710 providing high magnification optics, and a dark field illuminator 720 such as the multidirectional multispectral sleeve 100 of FIGS. 2-4B which typically fits over an objective lens 725 thereof such as a Leica 10×/0.3 objective. Preferably, a bright field illuminator 730, typically receiving polychromatic light from a polychromatic illumination source 732 via fiber optics 735, is also provided and a beam splitter 740 directs illumination from the bright field illuminator towards a workpiece (not shown) along an optical axis 790, while allowing the video camera to view the workpiece along the optical axis 790. Illumination may be provided either from the bright field illuminator 730, or from dark field illuminator 720, or from a combination of the two.

Figure 10:
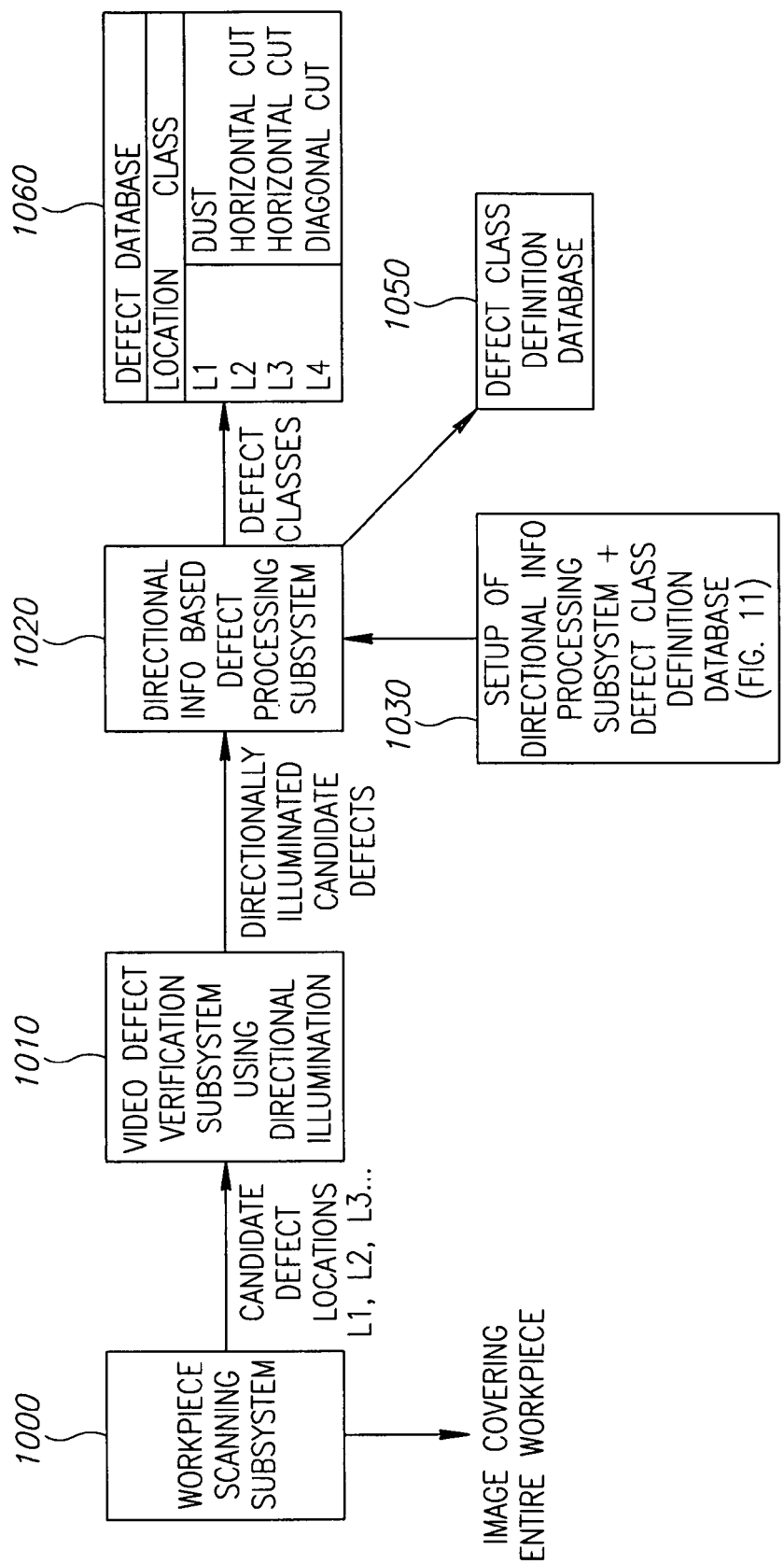
FIG. 10 is a simplified functional block diagram illustration of an automatic optical inspection system directionally illuminating at least candidate defect locations within a workpiece having microscopic features so as to categorize defects using directional information.

FIG. 10 is a simplified functional block diagram illustration of an automatic optical inspection system constructed and operative in accordance with a preferred embodiment of the present invention, to directionally illuminate at least candidate defect locations within a workpiece having microscopic features so as to categorize workpiece defects using directional illumination information. The automatic optical inspection system of FIG. 10 includes a workpiece scanning automated optical inspection subsystem 1000 such as a SuperVision™ system commercially available from Orbotech, Yavne, Israel, for scanning the workpiece and generating images covering substantially the entire workpiece. The workpiece scanning subsystem also preferably comprises an image processing functionality which is operative to identify candidate defects at specific workpiece locations L1, L2, L3, . . . . A multicolor direction specific video verification subsystem 1010 receives the candidate defect locations from the workpiece scanning subsystem 1000 and verifies the candidate defect locations by imaging these locations typically using dark field illumination and typically using a multicolor multidirectional optical head such as that of FIGS. 2-4B and 9 providing direction specific colored illumination. It is appreciated that subsystems 1000 and 1010 may be integrally formed, as in the SuperVision™ system, such that almost all components of the two subsystems and in particular the worktable and relative motion provider thereof, are shared, e.g. as shown in FIGS. 7A-7B.

Images of the directionally illuminated candidate defects are generated as aforesaid by the video verification subsystem using illumination that is offset from an optical axis and color-coded with reference to the direction from which it illuminates a candidate defect location; these images may be similar to those illustrated schematically in the tables of FIGS. 5A, 5B and 6. The directionally illuminated candidate defect images are fed to a directional information processing subsystem 1020, for example a video image processing package supplied with SuperVision™ automated optical inspection systems available from Orbotech Ltd. of Yavne, Israel. In an embodiment of the invention, the video image processing package includes a defect classification learning package which analyzes images with reference to a database 1050 of defect types defining classes of defects . Each new candidate defect is classified as a defect type to which it matches the closest, or by any other suitable criterion, or alternatively certain candidate defects are deemed non-defects such as foreign particles. The classification of the candidate defects is preferably stored in computer memory in a defect database 1060.

Figure 11:
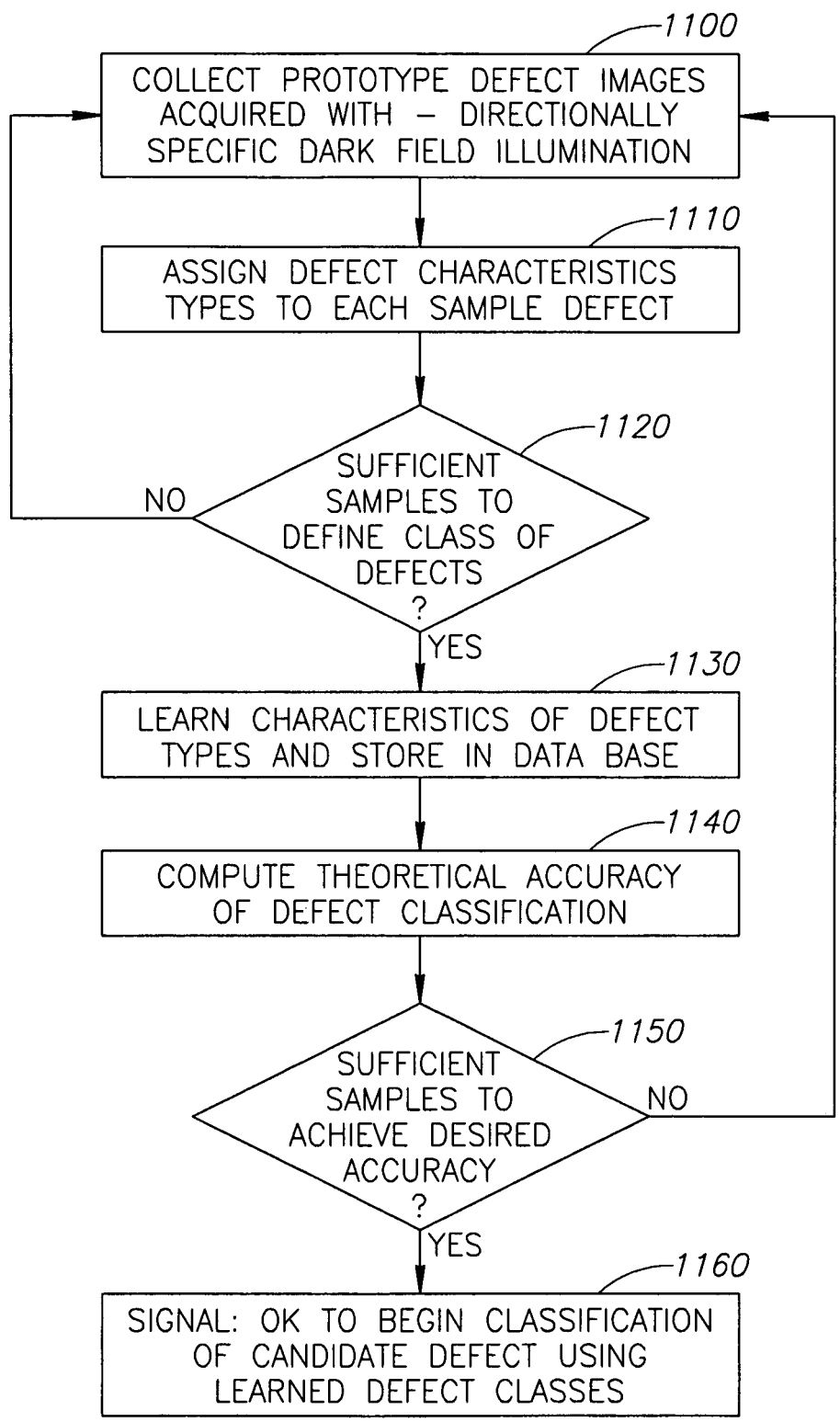
FIG. 11 is a simplified flowchart illustration of a preferred method of operation of the system of FIG. 10.

FIG. 11 is a simplified flowchart illustration of a method, performed by setup subsystem 1030, for setting up the directional information processing subsystem and defect class definition database 1050 of FIG. 10. In step 1100, the setup subsystem collects and analyzes prototype defects acquired by a video imager, such as at video defect verification subsystem 1010 under directionally specific illumination that is offset from an optical axis. In step 1110, each prototype or sample defect is assigned a defect type, for example a horizontal cut, vertical cut or dust. It is appreciated that the above defect type classifications are highly simplified and that in actuality there is likely to be a significantly greater number defect classification types and subtypes. Step 1120 checks that sufficient samples have accumulated to define each desired class of defects; if not, steps 1100 and 1110 are repeated until step 1120 is passed. In step 1130, defining characteristics of the defect types are learned and stored in defect class definition database 1050 of FIG. 10. The accuracy of the defect classification process is computed (step 1140) and step 1150 then checks whether a desired accuracy for defining a defect class has been reached. If not, the method returns to step 1100.

Once desired accuracy has been reached, the method signals that setup has been completed and that subsystem 1020 is now ready to commence classifying candidate defects using the learned defect types or categories stored in database 1050. It is noted that it is typically desired to improve the definition of defect classes in order to improve defect classification and in order to distinguish real defects that appear in the formation of a conductor, such as cuts and shorts, from candidate defects that are not actually defects such as foreign particles. Newly classified defects may be added to the defect data base to improve defect classification processes.

Figure 12:
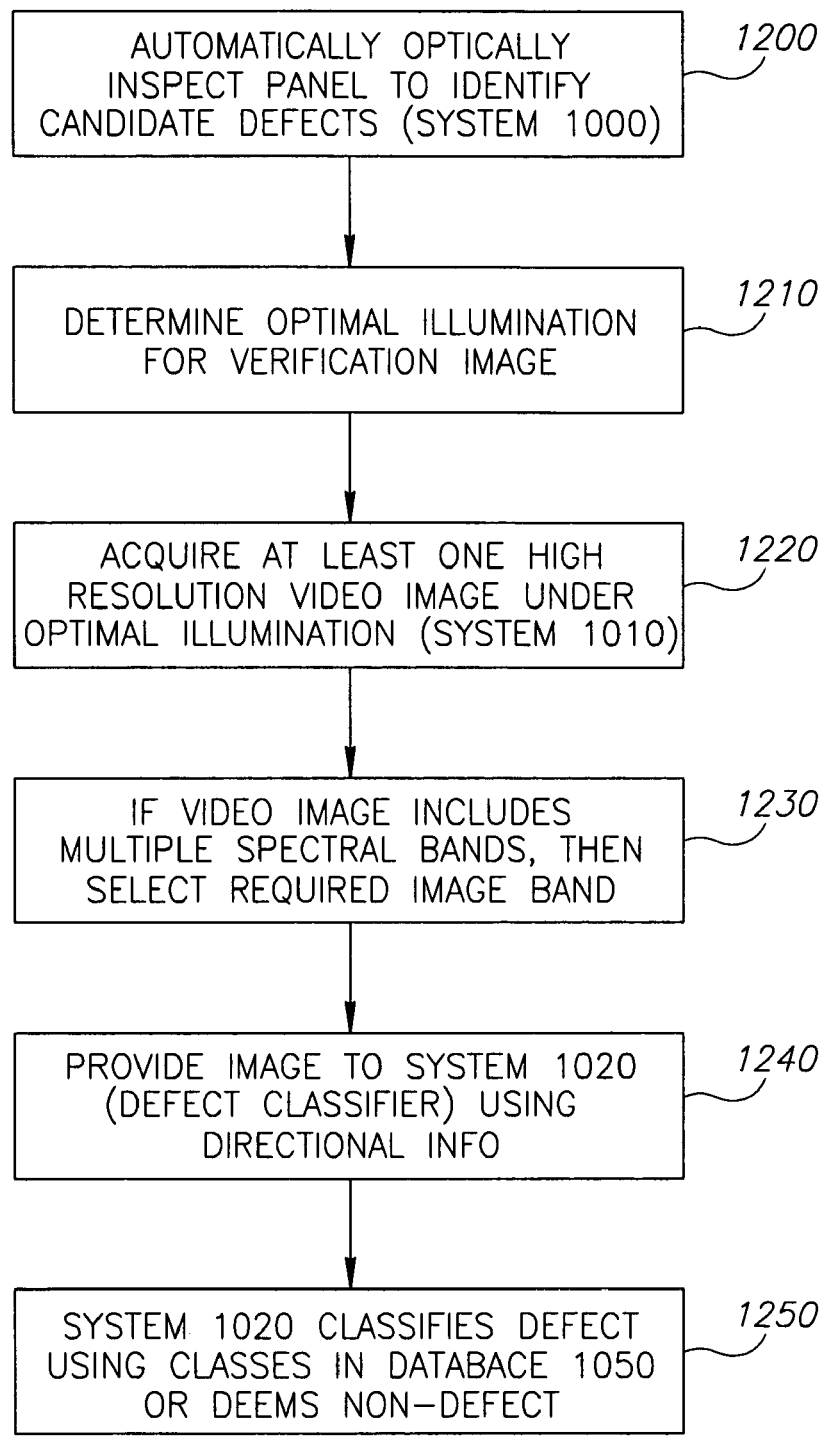
FIG. 12 is a simplified flowchart illustration of a preferred method for setting up the directional info processing subsystem of FIG. 10.

FIG. 12 is a simplified flowchart illustration of a method of operation of the system of FIG. 10. In step 1200, the workpiece scanning subsystem 1000 scans the workpiece and identifies candidate defect locations. In step 1210, at least one high resolution image video image is acquired under a first directionally specific illumination, and in step 1220 at least one high resolution image video image is acquired under a second directionally specific illumination. Alternatively, if a predominant direction of conductors is know at a given location, it may be sufficient to acquire only a single high resolution video image under a first directionally specific illumination. The first and second directionally specific illumination may be monochromatic or polychromatic, or the directionally specific illumination may include two or more differentiable forms of illumination in the same image, for example as described with reference to FIGS. 5A-6.

In step 1230, an optimal image is selected, for example an image in which proper conductor edges are dark and not seen, but in which defects are visible. In step 1240, at least one video image generated by subsystem 1010 is provided to the defect classifier of subsystem 1020. In step 1250, subsystem 1020 classifies candidate defects either as non-defects, for example as foreign particles that are on a surface or below a surface coating, or as defects of one class or another, using defect classes predefined by subsystem 1030 during set-up and stored in defect class definition database 1050.

One advantage of an embodiment of the present invention is that defect identification is facilitated by the fact that particles, due to a multiplicity of non-orderly edges, scatter light received from all directions thus resulting in a composite response of directionally specific light. Conversely, defects in the formation of a conductor, such as a cut or short, generally have a predominant direction and thus show a predominant response when illuminated by directionally specific illumination. When the directionally specific light is color coded, particles typically exhibit a multi-color response, while formation defects, that is defects in conductors, cuts, scratches, shorts and the like, exhibit a predominant color. Additionally, in accordance with an embodiment of the present invention, directionally specific illumination color coded with respect to a direction of illumination, enables the least number of images to be grabbed or acquired in the least time. Preferably, colors employed for imaging the candidate defects, such as red and blue, are such as to be completely separable (to within a noise level) by a color video camera.

It is appreciated that software components of the present invention may, if desired, by implemented in ROM (read only memory) form. The software components may, generally, be implemented in hardware, if desired, using conventional techniques.

Features of the present invention which are described in the context of separate embodiments may also be provided in combination in a single embodiment. Conversely, features of the invention which are described for brevity in the context of a single embodiment may be provided separately or in any suitable subcombination.

The invention claimed is:

1. An inspection system operative to inspect patterned devices having microscopic conductors, the system comprising:

at least first and second light sources, which illuminate a patterned substrate, said patterned substrate defining a substrate plane, wherein said first and second light sources define first and second paths of illumination, respectively; wherein said first and second paths of light are mutually non-parallel in a plane parallel to said substrate plane;

a camera viewing a location of a candidate defect on said patterned substrate, and acquiring thereat at least one image of the location, said at least one image being illuminated by illumination from at least said first and second light sources;

wherein said camera defines an optical axis and said first and second paths of illumination are offset from said optical axis; and wherein a response to illumination supplied along said first path of illumination is differentiable from a response to illumination supplied along said second path of illumination; and a defect classifier operative to receive said at least one image and to distinguish therewithin a candidate defect caused by a particle foreign to said patterned substrate from other types of candidate defects.

2. A system according to claim 1 and also comprising an automatic optical inspection device operative to supply locations of candidate defects to said camera.

3. A system according to claim 1 wherein said defect classifier is operative to identify defects caused by particles formed above a surface of said patterned substrate.

4. A system according to claim 1 wherein said defect classifier is operative to identify defects caused by particles formed under a coating within said patterned substrate.

5. A system according to claim 1 wherein said defect classifier is operative to identify defects caused by dust particles.

6. A system according to claim 1 wherein said illumination supplied along said first path differs in color from said illumination supplied along said second path.

7. A system according to claim 1 wherein said illumination supplied along said first path is supplied at a different time than said illumination supplied along said second path.

8. A system according to claim 1 wherein said first and second paths are perpendicular to each other.

9. A system according to claim 1 wherein least one of said first path and said second path has an angle of elevation which provides an average intensity for particles on said patterned substrate which is of the same order of magnitude as an average intensity for edges of microscopic conductors on said patterned substrate.

10. A system according to claim 1 wherein said patterned substrate comprises an in-fabrication display panel having conductors arranged in rows and in columns.

11. An inspection method operative to inspect patterned devices having microscopic conductors, the method comprising:
illuminating a patterned substrate, said patterned substrate defining a substrate plane, with illumination from at least first and second light sources defining first and second paths of illumination, respectively; wherein said first and second paths of illumination are mutually non-parallel in a plane parallel to said substrate plane;
viewing a location of a candidate defect on said patterned substrate, and acquiring thereat, with a camera, at least one image of said location, said at least one image being illuminated by illumination from at least said first and second light sources; wherein said camera defines an optical axis and said first and second paths of illumination are offset from said optical axis;
wherein a response to illumination supplied along said first path of illumination is differentiable from a response to illumination supplied along said second path of illumination; and
analyzing said at least one image to distinguish therewithin a candidate defect caused by a particle foreign to said patterned substrate from other types of candidate defects.

12. A method according to claim 11 wherein said illumination comprises dark field illumination.

13. A method according to claim 11 and also comprising supplying locations of candidate defects to said camera, using an automatic optical inspection device.

14. A method according to claim 11 wherein said analyzing said at least one image to distinguish comprises identifying defects caused by particles formed above a surface of said patterned substrate.

15. A method according to claim 11 wherein said analyzing said at least one image to distinguish comprises identifying defects caused by particles formed under a coating within said patterned substrate.

16. A method according to claim 11 wherein said analyzing said at least one image to distinguish comprises identifying defects caused by dust particles.

17. A method according to claim 11 wherein said illumination supplied along said first path differs in color from said illumination supplied along said second path.

18. A method according to claim 11 wherein said illumination supplied along said first path is supplied at a different time than said illumination supplied along said second path.

19. A method according to claim 11 wherein said first and second paths are perpendicular to each other.

20. A method according to claim 11 wherein at least one of said first path and said second path has an angle of elevation with respect to said patterned substrate which provides an average intensity for particles on said substrate which is of the same order of magnitude as an average intensity for edges of microscopic conductors on said patterned substrate.

21. A method according to claim 11 and also comprising providing said patterned substrate, wherein said patterned substrate comprises an in-fabrication display panel having conductors arranged in rows and in columns.

22. An inspection system operative to inspect patterned devices having microscopic conductors, the system comprising:
at least first and second light sources, which illuminate a patterned substrate, said patterned substrate defining a substrate plane, wherein said first and second light sources define first and second paths of illumination, respectively; wherein said first and second paths of illumination are mutually non-parallel in a plane parallel to said substrate plane;
a camera viewing a location of a candidate defect on said patterned substrate, and acquiring thereat at least one image of said location, said at least one image being illuminated by illumination from at least said first and second light sources;
wherein said camera defines an optical axis and said first and second paths of illumination are offset from said optical axis; and
wherein a response to illumination supplied along said first path of illumination is differentiable from a response to illumination supplied along said second path of illumination; and
a defect classifier operative to use said at least one image to distinguish a defect caused by a cut in an at least partially conductive area of said patterned substrate, from at least one other type of defect.

23. A system according to claim 22 wherein said defect classifier is also operative to use said at least one image to distinguish a foreign particle resting on said patterned substrate from at least one other type of defect.

24. A system according to claim 22 wherein said defect classifier is also operative to use said at least one image to distinguish excess material on said patterned substrate from at least one other type of defect.

25. A system according to claim 24 wherein said excess material comprises residue.

26. A system according to claim 22 wherein said at least partially conductive area comprises at least one conducting element.

27. A system according to claim 22 wherein said at least partially conductive area comprises at least one semi-conducting element.

28. A system according to claim 22 wherein said at least partially conductive area comprises a connection between a plurality of at least partially conducting elements.

29. A system according to claim 28 wherein said plurality of at least partially conducting elements comprises at least one conducting element.

30. A system according to claim 28 wherein said plurality of at least partially conducting elements comprises at least one semi-conducting element.

* * * * *